US011023979B2

(12) United States Patent
Taketomo

(10) Patent No.: US 11,023,979 B2
(45) Date of Patent: Jun. 1, 2021

(54) REFERENCE PRICE INDEX FOR PHARMACEUTICAL PRODUCTS

(71) Applicant: VENTEGRA, LLC., Glendale, CA (US)

(72) Inventor: Robert Taketomo, Houston, TX (US)

(73) Assignee: Ventegra, Inc., Glendale, CA (US)

( * ) Notice: Subject to any disclaimer, the term of this patent is extended or adjusted under 35 U.S.C. 154(b) by 490 days.

(21) Appl. No.: 14/223,623

(22) Filed: Mar. 24, 2014

(65) Prior Publication Data

US 2016/0027136 A1 Jan. 28, 2016

(51) Int. Cl.
G06Q 40/08 (2012.01)
G16H 70/40 (2018.01)
G06Q 10/10 (2012.01)
G16H 20/10 (2018.01)

(52) U.S. Cl.
CPC ............. *G06Q 40/08* (2013.01); *G06Q 10/10* (2013.01); *G16H 70/40* (2018.01); *G16H 20/10* (2018.01)

(58) Field of Classification Search
CPC ........ G06Q 50/22; G06Q 40/08; G06Q 10/10; G06F 19/328; G06F 19/3456; G16H 20/10; G16H 70/40
See application file for complete search history.

(56) References Cited

U.S. PATENT DOCUMENTS

| | | | |
|---|---|---|---|
| 7,438,218 B2 | 10/2008 | Dooley | |
| 8,335,695 B2 | 12/2012 | Cedergreen | |
| 2002/0002473 A1* | 1/2002 | Schrier | ................. G06F 19/326 705/3 |
| 2006/0184391 A1 | 8/2006 | Barre et al. | |
| 2009/0313039 A1* | 12/2009 | Cedergreen | ............ G06Q 30/02 705/2 |
| 2011/0119207 A1 | 5/2011 | Tong et al. | |
| 2012/0136809 A1* | 5/2012 | Cannata | ............. G06Q 30/0283 705/400 |
| 2012/0185263 A1 | 7/2012 | Emert | |
| 2012/0253829 A1 | 10/2012 | John | |

FOREIGN PATENT DOCUMENTS

KR 1020040089847 A 10/2004

OTHER PUBLICATIONS

Jang, Gijeong, International Search Report for PCT Application No. PCT/US15/17861 dated May 29, 2015.
Jang, Gijeong, Written Opinion for PCT Application No. PCT/US15/17861 dated May 29, 2015.

* cited by examiner

*Primary Examiner* — Linh Giang Le
(74) *Attorney, Agent, or Firm* — Locke Lord LLP

(57) ABSTRACT

A pharmacy care manager (PCM) uses a reference price for a given drug that reflects the actual cost and availability of the drug in the market. The PCM determines a reference price index (RPI) using drug pricing and availability data from drug manufacturers, wholesalers, pharmacies, and the like, updated on a daily basis. Drug identification data obtained from industry publishers allow pharmaceutical products from different sources to be cross referenced. The PCM then uses the RPI as the basis for the reference price, thereby removing any arbitrariness or inconsistency in the reference price. The reference price may then be applied to pay pharmacy claims and request reimbursements from plan clients. Such an arrangement reduces or eliminates any differences between payment of claims and reimbursement.

14 Claims, 9 Drawing Sheets

REFERENCE PRICE INDEX FOR PHARMACEUTICAL PRODUCTS

FIELD OF THE INVENTION

The exemplary embodiments disclosed herein relate generally to methods and systems for managing the cost of prescription drugs and other pharmaceutical products and, more specifically, to a method and system for determining a single reference price for a pharmaceutical product based upon the actual cost of the product and the availability of the product in the market.

BACKGROUND OF THE INVENTION

Recent advances in medical technology has benefited, extended, and enriched the lives of people everywhere. Prescription drugs in particular have made it possible for people to live longer, healthier, and more meaningful lives compared to previous generations. These advances come with a hefty price tag, however, as evident by the steep rise in healthcare cost over the last few years. According to some studies, the portion of the US economy devoted to healthcare has more than doubled in the last 40 years, increasing from about 7.2% in the year 1970 to about 17.9% in the year 2010.

Various efforts have been made to rein in the cost of healthcare. For example, health maintenance organizations (HMO) and similar managed healthcare plans have been formed to establish specific guidelines regarding the types of treatments doctors may provide to patients and under what conditions they may provide such treatments. These plans leverage their large membership to limit the amount doctors may charge for each type of treatment. The result has been a general slowing of the rise in healthcare cost for the members of the HMOs and similar plans.

Likewise, managed prescription drug plans run by pharmacy benefits managers (PBM) have also risen to rein in the cost of prescription drugs. These PBMs leverage the large purchasing capacity of the plan participants to limit the amount that pharmacies may charge for prescription drugs. In a typical arrangement, a doctor prescribes a drug to a patient, who then goes to a pharmacy to fill the prescription. The pharmacy charges the patient a fixed co-pay amount, then submits a claim for the cost of the prescription drug to the PBM. The PBM pays the pharmacy a predetermined price for the drug, then requests reimbursement from its clients, including private employers, government agencies (e.g., Medicaid, Medicare), health insurers, and the like. In some instances, the PBM and/or the plan clients may also receive rebates from the drug manufacturers, typically pharmaceutical companies, based on the volume of claims submitted for the drugs manufactured by those companies.

A drawback of existing PBMs is they lack a clear, objective, and quantifiable way to determine which price should be paid to the pharmacies for a given drug and which price should be charged to the plan clients. The prices used often depend on a number of cost factors, including the Average Wholesale Price ("AWP"), Wholesale Acquisition Cost ("WAC"), Maximum Allowable Cost ("MAC"), and Usual & Customary ("U&C") charge. The Federal government has also attempted to develop some measure of drug cost: Average Sales Price ("ASP") and Average Manufacturer Price "AMP." As explained below, however, there is currently no uniform way to determine and apply these cost factors.

AWP is a benchmark that is widely used for pricing and reimbursement of prescription drugs for both government and private payers. This average has often been compared to the "list price" or "sticker price" of a drug, meaning it is an elevated drug price that is rarely what is actually paid. The "average" in AWP may be calculated as a mean, or a median, or a mode, and is affected by which "wholesale price" is used as a reference (there is no officially-recognized wholesale price list). Thus, there may be numerous AWP's for the same drug, and the updates are arbitrary.

Similarly, WAC represents a manufacturer's catalog or list price for a drug as sold to wholesalers. This cost does not represent actual transaction costs and does not include discounts, rebates, or other reductions in price. The "wholesale" in WAC could represent any arbitrary cost figure at which a given manufacturer decides to sell its drug products. There are numerous WAC's possible for the same drug and revisions in WAC are arbitrary.

Likewise, the "maximum" in MAC is an arbitrary figure usually defined by the PBM. The PBM may have different MAC prices for the same drug—one MAC price for pharmacies and another, higher MAC price for PBM clients. The difference or "spread" in MAC prices becomes revenue for the PBM.

The attempts by the Federal government to determine drug cost has resulted in formulaic solutions that attempt to use pricing information from pharmaceutical manufacturers ("the source"): ASP and AMP. However, these solutions are compromised by the fact that they do not reflect retail market conditions (e.g., the cost after the drug passes through the supply chain), the calculations have been "modified" by various adjustments, inclusions and exclusions, and are still calculated "averages" released on some periodic basis (usually calendar quarter which, in practice, lags the market conditions by about 5-6 months).

Finally, the usual and customary charge in U&C is an arbitrary charge (not cost) that is established by pharmacies. A given pharmacy may apply multiple U&C calculations to the same drug in an arbitrary manner.

A need therefore exists for an improved way to manage the cost of prescription drugs and other pharmaceutical products and, in particular, a need exists for a way to determine a single price for the pharmaceutical product based on the actual acquisition cost of the product and the availability of the product in the market.

SUMMARY OF THE INVENTION

The exemplary embodiments disclosed herein relate to a method and system for implementing an improved pharmacy benefits manager that, for convenience, is referred to herein as a pharmacy care manager (PCM). The PCM provides a number of important advantages over existing PBMs, including the use of a reference price index (RPI) as the basis for a reference price for a given pharmaceutical product (which could be branded as an "Acquisition Cost Index"). This reference price reflects the actual cost of the product and the number of units of the product available in the market, thereby removing the arbitrariness and inconsistency of prior solutions. In some embodiments, the PCM may apply a cost adjustment factor to the RPI to account for discounts receive by the supply chain (e.g., wholesaler, distributor or pharmacy), for example, before using it as the basis for the reference price. Similarly, in some embodiments, the PCM may apply a packaging adjustment factor to the RPI to account for any differences, for example, in package size and other variations among product sources. In some embodiments, the RPI is calculated automatically every 24 hours, and is available for uploading and use by prescription pricing claim systems on this frequency. This allows the RPI to reflect true market conditions and availability of prescription drug products in the market. This is especially pertinent when drug supply is sporadic or there are shortages or excess in the market. The RPI is adjusted quickly, objectively and quantitatively to reflect these market conditions.

Once the reference price for a given pharmaceutical product has been determined, the PCM may use the reference price to pay participating pharmacies for the product, including retail, specialty, and mail order pharmacies as well as medical services providers. As well, the PCM may use this reference price to request reimbursement from PCM clients for the product. The RPI and hence the reference price may be automatically recalculated on a regular basis, such as daily, to reflect any changes in market conditions. This allows the system, method, and computer program product disclosed herein to more accurately track the true market availability of the pharmaceutical product. As a result, there is little to no difference or "spread" between the prices the PCM pays to the pharmacies and the prices the PCM submits to plan clients for reimbursement. Note that while the RPI provides a more accurate calculation of market pricing, depending on the implementation, it is of course possible for the PCM selectively to apply some level of spread pricing for certain clients without departing from the scope of the disclosed embodiments.

In general, in one aspect, the exemplary disclosed embodiments relate to a computer-based system for implementing a PCM. The system comprises, among other things, a central processing unit mounted within the computer-based system, a display electrically connected to the central processing unit and displaying reference prices for pharmaceutical products managed by the PCM. The system additionally comprises a data input unit in data communication with the central processing unit, the data input unit receiving pricing and availability data for the pharmaceutical products from multiple distributors of the pharmaceutical products, the pricing and availability data including a cost and a quantity available for each pharmaceutical product from each distributor, the data input unit further receiving identification data for the pharmaceutical products from a publisher of the identification data. The system further comprises a storage device in data communication with the central processing unit, the storage device storing a PCM application 318 executable by the central processing unit to calculate an RPI for each pharmaceutical product from the pricing and availability data for the pharmaceutical product, the PCM application 318 executable by the central processing unit to use the RPI as a basis to establish a reference price for the pharmaceutical product. The reference price for each pharmaceutical product may then be used by the PCM to pay pharmacy claims for the pharmaceutical product and submit reimbursement requests for the pharmaceutical product.

In general, in another aspect, the exemplary disclosed embodiments relate to a computer-based method for implementing a PCM. The method comprises, among other things, receiving pricing and availability data for pharmaceutical products from multiple distributors of the pharmaceutical products through a data input unit in communication with a central processing unit, the pricing and availability data including a cost and a quantity available for each pharmaceutical product from each distributor. The method also comprises receiving identification data for the pharmaceutical products from a publisher of the identification data through the data input unit in communication with the central processing unit. The method further comprises using the central processing unit to read a PCM application 318 stored on a data storage unit and execute the PCM application 318 to calculate an RPI for each pharmaceutical product from the pricing and availability data for the pharmaceutical product, the central processing unit executing the PCM application 318 to use the RPI as a basis to establish a reference price for the pharmaceutical product. The reference price for each pharmaceutical product may then be used by the PCM to pay pharmacy claims for the pharmaceutical product and submit reimbursement requests for the pharmaceutical product.

In general, in yet another aspect, the exemplary disclosed embodiments relate to a computer-readable medium storing computer-readable instructions for causing a computer to implement a PCM. The computer-readable instructions comprise instructions for causing the computer to, among other things, receive pricing and availability data for pharmaceutical products from multiple distributors of the pharmaceutical products, the pricing and availability data including a cost and a quantity available for each pharmaceutical product from each distributor. The computer-readable instructions also comprise instructions for causing the computer to receive identification data for the pharmaceutical products from a publisher of the identification data. The computer-readable instructions further comprise instructions for causing the computer to calculate an RPI for each pharmaceutical product from the pricing and availability data for the pharmaceutical product and use the RPI as a basis to establish a reference price for the pharmaceutical product. The reference price for each pharmaceutical product may then be used by the PCM to pay pharmacy claims for the pharmaceutical product and submit reimbursement requests for the pharmaceutical product.

BRIEF DESCRIPTION OF THE DRAWINGS

The foregoing and other advantages of the exemplary disclosed embodiments will become apparent upon reading the following detailed description and upon reference to the drawings, wherein.

DETAILED DESCRIPTION OF THE DISCLOSED EMBODIMENTS

As an initial matter, it will be appreciated that the development of an actual, real commercial application incorporating aspects of the exemplary disclosed embodiments will require many implementation specific decisions to achieve the developer's ultimate goal for the commercial embodiment. Such implementation specific decisions may include, and likely are not limited to, compliance with system related, business related, government related and other constraints, which may vary by specific implementation, location and from time to time. While a developer's efforts might be complex and time consuming in an absolute sense, such efforts would nevertheless be a routine undertaking for those of skill in this art having the benefit of this disclosure.

It should also be understood that the embodiments disclosed and taught herein are susceptible to numerous and various modifications and alternative forms. Thus, the use of a singular term, such as, but not limited to, "a" and the like, is not intended as limiting of the number of items. Similarly, any relational terms, such as, but not limited to, "top," "bottom," "left," "right," "upper," "lower," "down," "up," "side," and the like, used in the written description are for clarity in specific reference to the drawings and are not intended to limit the scope of the invention.

Figure 1:
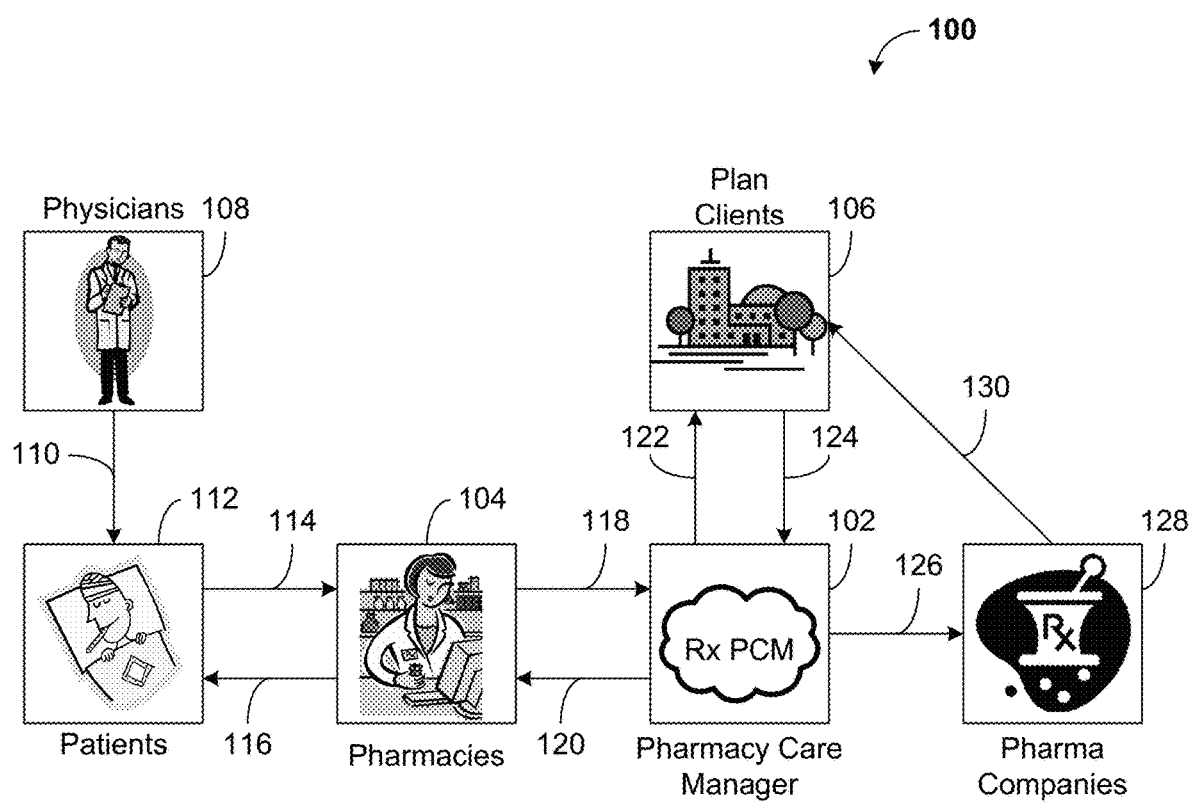
FIG. 1 is an example of managed prescription drug plan employing the PCM concepts disclosed herein according to the exemplary disclosed embodiments.

Turning now to FIG. 1, the exemplary disclosed embodiments relate to a computer-implemented method, system, and computer program product for implementing a pharmacy care manager (PCM). One advantage of the PCM over prior solutions is the use of a reference price index (RPI) as the basis for a reference price for a given pharmaceutical product. This RPI is in essence a weighted cost that reflects the actual cost of the pharmaceutical product and the availability of the product in the market. The RPI is updated on a regular basis (e.g., hourly, daily, weekly, etc.). In some embodiments, the PCM may apply a cost adjustment factor to the RPI in order to accurately account for discounts being offered to intermediary distributors or pharmacies. Similarly, in some embodiments, the PCM may apply a packaging adjustment factor to the RPI to account for any differences, for example, in package size and other variations among product sources.

It should be noted that although the exemplary disclosed embodiments may sometimes appear to focus on prescription drugs, the inventive concepts described herein are equally applicable to all types of pharmaceutical products, including non-prescription drugs (i.e., over-the-counter drugs), brand name and generic drugs, specialty drugs, neutraceuticals (e.g., vitamins, supplements, etc.), and the like. All of these pharmaceutical products are considered to be within the scope of the exemplary disclosed embodiments and are interchangeably referenced in this description as "drugs." These drugs may be obtained from any number of available sources in the market, including drug manufacturers, drug wholesalers, pharmacies, and the like, all of which are generally referred to herein as "distributors" for convenience. Information regarding these drugs, including, the drug name, strength, dosage, package size, and the like, are available from industry sources generally referred to herein as "publishers."

As FIG. 1 shows, a managed prescription drug plan 100 according to the disclosed embodiments may include a PCM 102, a network of pharmacies 104, and one or more plan clients 106 (e.g., employers, government agencies, health insurers, etc.). In a typical scenario, upon completion of a diagnosis, a physician 108 writes a prescription 110 for one of his/her patients 112. The patient 112 takes the prescription 110 to one of the pharmacies 104 where he/she makes a fixed copayment 114. The pharmacy 104 provides the prescribed drug 116 to the patient 112 and thereafter submits a claim 118 to the PCM 102 for payment of the drug 116. At this point, whereas existing PBMs would pay a price that depended on several arbitrarily determined cost figures, the PCM 102 uses a reference price for the prescribed drug 116 that reflects the actual cost of the drug and the availability of the drug in the market. The PCM 102 makes a payment 120 to the pharmacy 104 equal to the reference price, submits a reimbursement request 120 to the appropriate plan client 106 for this reference price, and receives a reimbursement 124 from the plan client 106 equal to the reference price. This results in little to no difference or "spread" in the payment 120 to the pharmacy 104 and the reimbursement 124 from the plan client 106. The PCM 102 makes revenue through a transparent fee-for-service arrangement instead.

In some cases, the PCM 102 may also charge the plan client 106 a small administrative fee and/or service related fee for processing the claim related to the prescribed drug 116. As well, the PCM 102 may provide claims related data 126 to one or more pharmaceutical companies 128 for evaluation purposes. If the pharmaceutical companies 128 offer any rebates and/or discounts 130 based on the claims related data 126, such rebates and/or discounts 130 are provided directly to the plan clients 106.

Figure 2:
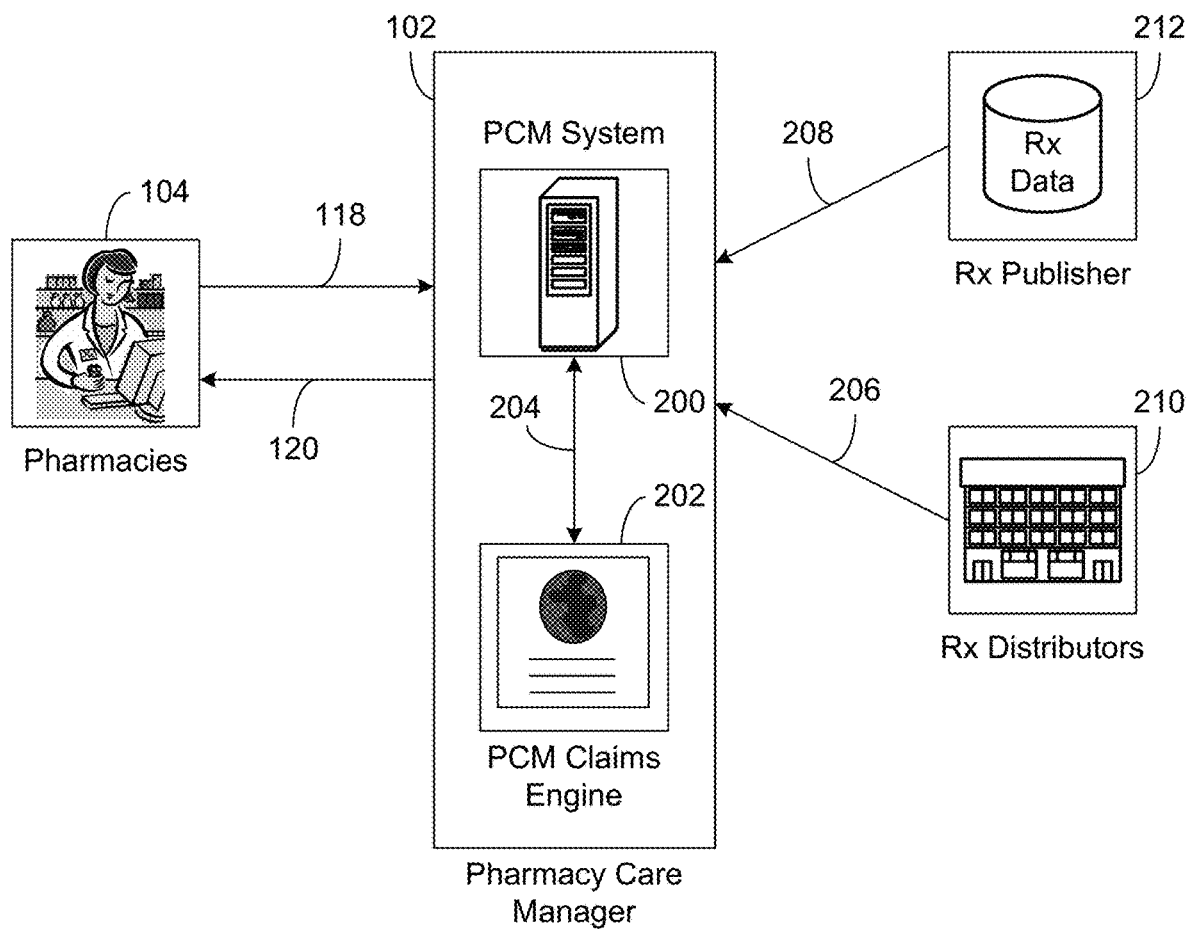
FIG. 2 is an example of a PCM network that may be used to implement the PCM according to the exemplary disclosed embodiments.

FIG. 2 illustrates the PCM 102 in more detail according to the exemplary disclosed embodiments. As can be seen, the PCM 102 may be composed of a PCM system 200 connected to a PCM claims engine 202 over a network connection 204. In general, the PCM system 200 performs the back end data processing needed for the PCM 102 to determine the reference prices, while the PCM claims engine 202 performs the front end data processing needed for adjudicating claims from the pharmacies 104. In accordance with the exemplary disclosed embodiments, the PCM claims engine 202 uses the reference prices from the PCM system 200, which are uploaded on a regular basis, to adjudicate the claims from the pharmacies 104. Any suitable claims engine known to those having ordinary skill in the art may be used as the PCM claims engine 202, the technical aspects of the PCM claims engine 202 being less important to the exemplary disclosed embodiments. Similarly, the network connection 204 may be any suitable private or public network connection that allows the PCM system 202 to upload the reference prices to the PCM claims engine 202. Preferably the PCM system 200 uploads the reference prices and other necessary information to the PCM claims engine 202 on a daily basis, but a different schedule may certainly be used as needed (e.g., twice daily, weekly, twice weekly, bi-weekly, etc.).

Also shown in FIG. 2 are the data sources from which the PCM system 200 obtains the data used to determine the reference prices. In general, there are two types of data the PCM system 200 uses to determine the reference prices: drug pricing and availability data 206 and drug identification data 208. The drug pricing and availability data 206 is usually provided by distributors 210 and allow the PCM system 200 to obtain the current cost of drugs in the market, while the drug identification data 208 is usually provided by publishers 212 and allows the PCM system 200 to cross reference the various drugs available in the market to one another. An example of a suitable distributor 210 that can provide drug pricing and availability data 206 is AmerisourceBergen Corporation of Chesterbrook, Pa. Other suitable distributors may include Cardinal Health of Dublin, Ohio, McKesson Pharmaceutical of San Francisco, Calif., and the like. An example of a suitable publisher that can provide drug identification data 208 is Medi-Span of Indianapolis, Ind.

Figure 3:
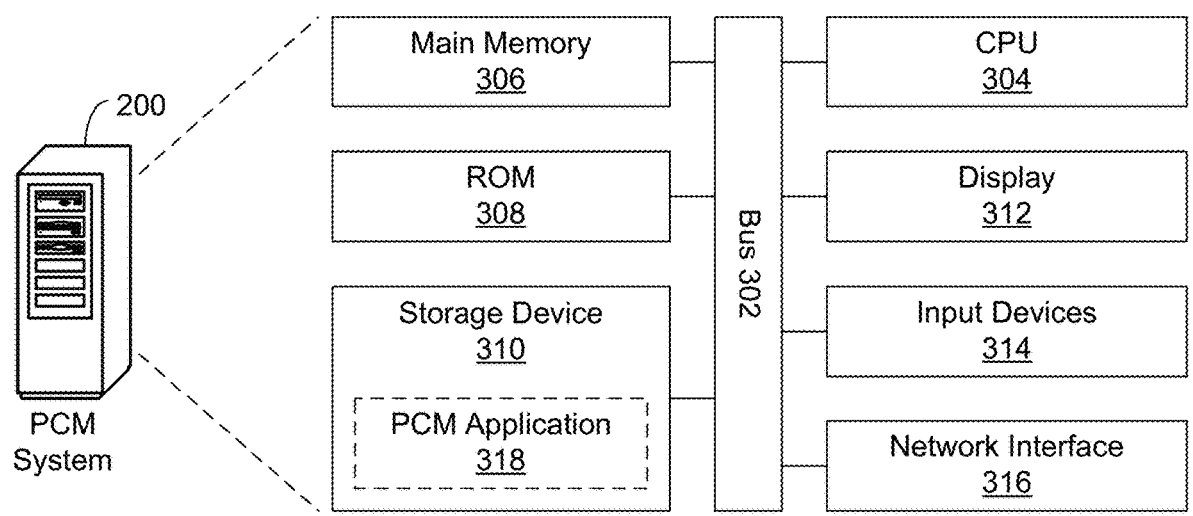
FIG. 3 is an example of a PCM system that may be used to implement the PCM according to the exemplary disclosed embodiments.

FIG. 3 illustrates additional details of the PCM system 200. As can be seen, the exemplary PCM system 200 may be a conventional workstation, desktop, or laptop computer, or it may be a custom computing system developed for a particular application. In a typical arrangement, the system 200 includes a bus 302 or other communication pathway for transferring information within the PCM system 200, and a CPU 304 coupled with the bus 302 for processing the information. The PCM system 200 may also include a main memory 306, such as a random access memory (RAM) or other dynamic storage device coupled to the bus 302 for storing computer-readable instructions to be executed by the CPU 304. The main memory 306 may also be used for storing temporary variables or other intermediate information during execution of the instructions to be executed by the CPU 304. The PCM system 200 may further include a read-only memory (ROM) 308 or other static storage device coupled to the bus 302 for storing static information and instructions for the CPU 304. A computer-readable storage device 310, such as a nonvolatile memory (e.g., Flash memory) drive or magnetic disk, may be coupled to the bus 302 for storing information and instructions for the CPU 304. The CPU 304 may also be coupled via the bus 302 to a display 312 for displaying information to a user. One or more input devices 314, including alphanumeric and other keyboards, mouse, trackball, cursor direction keys, and so forth, may be coupled to the bus 302 for communicating information and command selections to the CPU 304. A communications interface 316 may be provided for allowing the PCM system 200 to communicate with an external system or network.

The term "computer-readable instructions" as used above refers to any instructions that may be performed by the CPU 304 and/or other components. Similarly, the term "computer-readable medium" refers to any storage medium that may be used to store the computer-readable instructions. Such a medium may take many forms, including, but not limited to, non-volatile media, volatile media, and transmission media. Non-volatile media may include, for example, optical or magnetic disks, such as the storage device 310. Volatile media may include dynamic memory, such as main memory 306. Transmission media may include coaxial cables, copper wire and fiber optics, including wires of the bus 302. Transmission itself may take the form of electromagnetic, acoustic or light waves, such as those generated during radio frequency (RF) and infrared (IR) data communications. Common forms of computer-readable media may include, for example, magnetic medium, optical medium, memory chip, and any other medium from which a computer can read.

A PCM application 318, or rather the computer-readable instructions therefor, may also reside on or be downloaded to the storage device 310. In general, the PCM application 318 is or includes a computer program that can process drug pricing and availability data to calculate a reference price for a given drug. The PCM application 318 may be executed by the CPU 304 and/or other components of the PCM system 200 automatically, but may also be run manually by a user on an as-needed basis. Such a PCM application 318 may be implemented in any suitable computer programming language or software development package known to those having ordinary skill in the art. Examples may include C, C++, C#, FORTRAN, Microsoft Access, Microsoft SQL Server Reporting Services (SSRS), Microsoft SQL Server Integration Services (SSIS), and the like.

Figure 4:
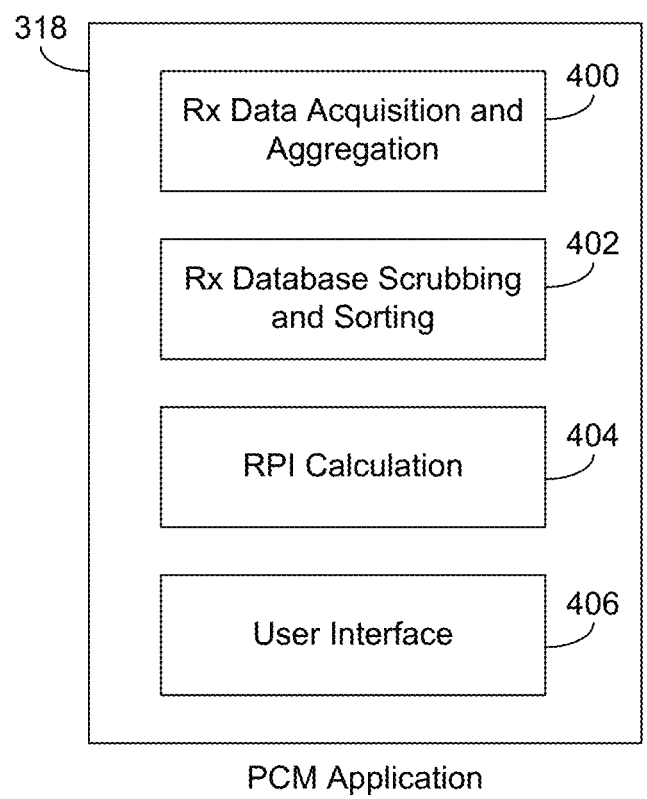
FIG. 4 is an example of a PCM application 318 that may be used to implement the PCM according to the exemplary disclosed embodiments.

FIG. 4 illustrates the PCM application 318 in more detail according to the embodiments disclosed herein. As can be seen, the PCM application 318 is composed of several functional components that may be software, hardware, or a combination of both, depending on the particular implementation. These functional components may include a drug data acquisition and aggregation component 400, a drug database scrubbing and sorting component 402, an RPI calculation component 404, and a user interface component 406. In general, the drug data acquisition and aggregation component 400 operates to acquire the drug pricing and availability data and drug identification data mentioned earlier. This component also combines the drug pricing and availability data from various distributors into a single aggregated database. The drug database scrubbing and sorting component 402 operates to filter the aggregated drug pricing and availability database and remove any unwanted or unneeded data, and sort the data in the database into specific groups depending on the implementation. The RPI calculation component 404 uses the scrubbed and sorted pricing and availability data to generate an RPI that may then be used to determine a reference price for the drugs in the database. Finally, the user interface component 406 provides a graphical interface for users to interact with the PCM application 318.

Figure 5:
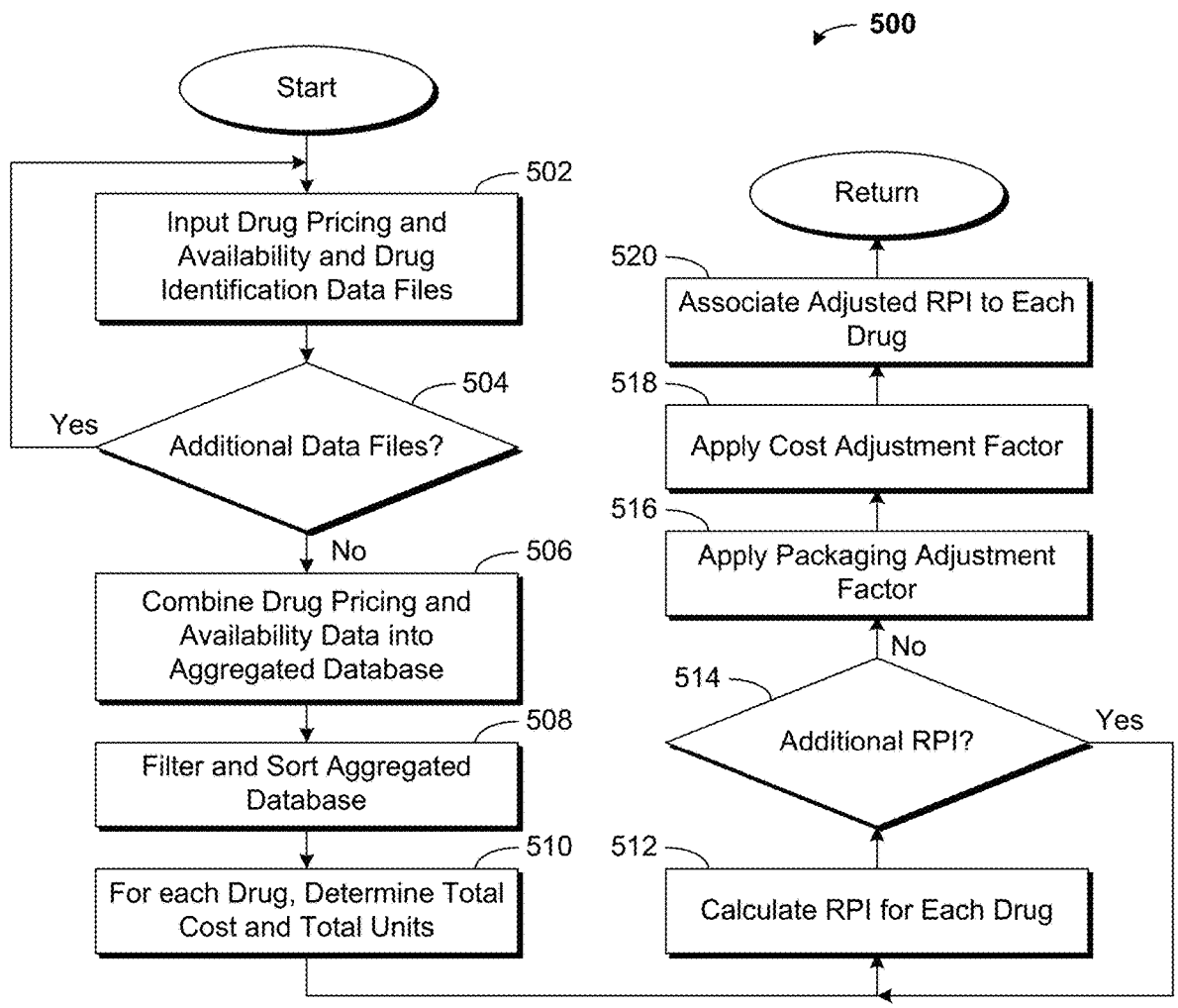
FIG. 5 is an example of a flowchart that may be used to implement the PCM according to the exemplary disclosed embodiments.

General operation of the PCM application 318, and the modules 400-406 therein, is depicted in FIG. 5 via a flow chart 500. Although the flow chart 500 shows a number of discrete blocks, it should be understood that any block may be divided into two or more constituent blocks, and that two or more blocks may be combined into a single block, without departing from the scope of the exemplary disclosed embodiments. Also, although the various blocks are arranged in a particular sequence in FIG. 5, it should be understood that one or more of the blocks may be performed outside the sequence shown, or omitted altogether in some cases, without departing from the scope of the exemplary disclosed embodiments.

As can be seen in FIG. 5, in general, the flow chart 500 begins at block 502, where data files are inputted to the PCM application 318. The data files may include the drug pricing and availability data and the drug identification data mentioned earlier. These data files may be in any suitable format, including text files, spreadsheets, XML files, and the like. Input may be accomplished by any suitable technique known to those having ordinary skill in the art, including downloading the data files over a network connection (e.g., FTP, HTTP, Telnet, etc.), direct transfer of the data files from an external source (e.g., CD, DVD, Flash drive, etc.), and even manual entry in some cases, without departing from the scope of the exemplary disclosed embodiments. And although daily inputs are preferred, the data files may be inputted according to any suitable schedule, regular or otherwise, including hourly, daily, weekly, monthly, and so forth.

At block 504, a determination is made whether additional data files need to be inputted. If the determination is yes, then the additional data files are inputted at block 502. If the determination is no, then the flow chart 500 proceeds to block 506, where the drug pricing and availability data files are combined into a single aggregated database. At block 508, the aggregated database is filtered to remove any unwanted or unneeded data, and the remaining data is sorted into groups as needed, depending on the particular implementation of the PCM application 318. For example, the aggregated database may be sorted by brand name versus generic drugs, by individual drugs (or drug type), and the like. At block 510, the total cost and total number of units is tallied for each individual drug (or drug type). An RPI for each individual drug (or drug type) is thereafter calculated at block 512 using the total costs and total number of units. A number of ways exists for calculating the RPI, but in some embodiment, the RPI may be calculated by dividing the total cost by the total number of units for each individual drug (or drug type).

At block 514, a determination is made whether additional drugs (or drug types) need to have an RPI calculated. If the determination is yes, then the flow chart 500 returns to block 512 to calculate additional RPIs. If the determination is no, then at block 516, a packaging adjustment factor is applied to the RPIs to account for any differences in drug package size or other variations among the different distributors. The default packaging adjustment factor is 1 (i.e., no adjustment) based on a presumption that there are no discrepancies in how package sizes are interpreted or other variations for a given drug (or drug type). This packaging adjustment factor may be applied automatically by the PCM application 318, or it may be applied manually by a user via the user interface component 408, or both.

Similarly, at block 518, a cost adjustment factor is applied to the RPIs to account for any additional discounts on drugs provided to the distributors. The default cost adjustment factor is also 1 (i.e., no adjustment) based on a presumption that no fine-tuning is needed for the total cost for the various drugs (or drug types). Again, this cost adjustment factor may be applied automatically by the PCM application 318, or it may be applied manually by a user via the user interface component 408, or both.

Thereafter, at block 518, each RPI (including any adjustments made thereto) is associated with its respective drug (or drug type). The RPI (including any adjustments made thereto) may then be used as the reference price for each drug (or drug type) accordingly.

Following now is an example of a specific implementation of the PCM application 318 according to the exemplary embodiments disclosed herein. In this implementation, the PCM application 318 is set up to receive the following pricing and availability data: Source Identifier, Date of Data Importation, National Drug Code (NDC), Quantity on Hand (QOH), Actual Acquisition Cost (AAC), Wholesale Acquisition Cost (WAC), and Average Wholesale Price (AWP). In general, Source Identifier is a numeric or alphanumeric code that identifies the distributor providing the data, such as AmerisourceBergen, or Cardinal Health, or McKesson, among others. Date of Data Importation, as the name suggests, is the date the drug data was inputted. National Drug Code (NDC) is a unique 11-digit product identifier assigned by the Food and Drug Administration (FDA) when a new drug is registered with the FDA. Quantity on Hand (QOH) is the number of packages of a given drug available in the inventory of the distributor providing the data. AAC is the net cost of a drug paid by a pharmacy and may vary with the size of the package (e.g., ten bottles of 100 tablets typically costs more than one bottle of 1,000 tablets). WAC and AWP include arbitrary pricing components that were described previously. Table 1 below shows the field names used by the PCM application 318 for the pricing and availability data and their corresponding data types.

TABLE 1

Drug Pricing and Availability Data

| Field Name | Data Type |
| --- | --- |
| Source Identifier | Text |
| Date of Data Importation | Date |
| National Drug Code (NDC) | Text |
| Quantity on Hand (QOH) | Decimal |
| Actual Acquisition Cost | Currency |
| Wholesale Acquisition Cost | Currency |
| Average Wholesale Price | Currency |

In addition to the pricing and availability data, the PCM application 318 is also designed to use the following drug identification data: National Drug Code (NDC), Generic Product Identifier (GPI), Package Size, Drug Label, Generic Name, Strength, Dosage Form, and Brand/Generic indicator. The National Drug Code (NDC) is again the unique product identifier assigned by the FDA. The Generic Product Identifier (GPI) is a 14-digit code assigned by Medi-Span to drugs that are considered to be pharmaceutically equivalent with respect to their active ingredients, dosage form, route of administration, strength, and the like. The Package Size specifies the number of units of a given drug per package. The Drug Label specifies the trade name of the drug, the Generic Name specifies the common name of the drug, the Strength specifies the amount of drug in a given dosage, and the Dosage Form specifies the means by which the drug is administered (e.g., capsule, tablet, liquid, etc.). The Brand/Generic indicator identifies whether the drug is a brand-name or a generic drug. This drug identification data may be obtained from drug data publishers such as Medi-Span among others and allows the PCM application 318 to cross reference equivalent drugs from multiple different distributors. In some embodiments, a flag or other indicator may also be provided to signal whether a given drug is a prescription drug or an over-the-counter (OTC) drug. Table 2 below shows the field names used by the PCM application 318 for the drug identification data and their corresponding data types.

TABLE 2

Drug Identification Data

| Field Name | Data Type |
| --- | --- |
| National Drug Code (NDC) | Text |
| Generic Product Identifier (GPI) | Text |
| Package Size (units/package) | Decimal |
| Drug Label (trade name) | Text |
| Generic Name | Text |
| Strength | Text |
| Dosage Form | Text |
| Brand/Generic | Text |
| Rx/OTC | Text |

It should be understood that the data listed in Tables 1 and 2 are exemplary only and neither table is exclusive or exhaustive. Thus, some of the data in the tables may be omitted from the PCM application 318, while other data added to the PCM application 318, or both, without departing from the scope of the disclosed embodiments. For example, the ACC application may operate without the prescription versus over-the-counter drugs field shown in the last row of Table 2. Alternatively, instead of the Brand/Generic indicator field, the PCM application 318 may use data pertaining to whether a given drug is single-sourced or multi-sourced. Other data fields not shown in Tables 1 and 2 that may be used by the PCM application 318 may include a Stock Keeping Unit (SKU) field. Of course, the specific data used by the PCM application 318 will depend in large part on the availability of that data from participating distributors and publishers. It is also possible to update which data is used by the PCM application 318 from time to time as may be needed to reflect advances in technology, changing market conditions, and the like.

Once the drug pricing and availability data and the drug identification data are obtained, the PCM application 318 may begin processing the data. To facilitate data processing, the drug pricing and availability data from the various distributors may be collected and combined or otherwise aggregated into a single database. It is suggested that the NDC data field be used to index this aggregated pricing and availability database for obvious reasons, but adding a separate Index field to the database is certainly an option as well. Next, the database should be filtered and/or scrubbed to remove any unwanted or unneeded data depending on the implementation. For example, the database may be filtered and/or scrubbed to remove data pertaining to over-the-counter drugs, durable medical supplies (e.g., batteries, wheelchairs, canes, diapers, etc.), and the like. Any data that is duplicative or redundant of existing data, such as per unit dose data (which is included in the drug identification data), may also be removed.

The PCM application 318 then uses the remaining data in the aggregated drug pricing and availability database along with other data to determine an RPI for each drug in the database. This RPI may be determined in a number of ways depending on the specific implementation. For example, the PCM application 318 may segregate the pricing and availability database into two groups, a brand-name group and a generic group, then determine the RPI for each drug in each group separately. This approach results in a brand-name RPI and a generic RPI for each drug. Alternatively, the PCM application 318 may forgo the brand-name versus generic distinction and simply determine one RPI for each drug in the whole database.

Where the brand-name versus generic distinction is desired, the PCM application 318 may sort the database according to the Brand/Generic indicator field (see Table 2). This sorting divides the database into a brand-name group and generic group. From these two groups, the PCM application 318 may create two tables, a brand-name drugs table and a generic drugs table. To further facilitate calculating the RPI, the PCM application 318 may sort each table by the GPI field (see Table 2). This further sorting results in the same or similar drugs being grouped together within each table according to their GPIs. The PCM application 318 may thereafter use the sorted tables to calculate the RPI for brand-name drugs and generic drugs according to their GPIs. The RPI may then be used as the basis for the reference price for each brand-name and generic drug according to their GPIs.

A number of ways exists for the PCM application 318 to calculate the RPI, which is essentially a weighted cost. In the exemplary implementation discussed here, the PCM application 318 may calculate the RPI or weighted cost by adding up the cost figures mentioned previously to obtain a total cost, then dividing the total cost by the total number of units. For example, for a given GPI, the RPI may be calculated by adding the WAC or AWP for that GPI, then dividing by the total QOH times the Package Size (see Table 1) for that GPI. Alternatively, the RPI may be calculated by adding the AAC, WAC, or AWP for the GPI, then dividing by the total QOH times the Package Size for that GPI. Any suitable algorithm, routine, or process may be used to calculate the RPI described without departing from the scope of the exemplary disclosed embodiments, as the specific sequence of steps is not critical to the practice of the exemplary disclosed embodiments. One example of an algorithm, routine, or process for calculating the RPI is provided in the form of pseudocode below:

```
Initialize RPI Units      [Array for accumulating total units]
Initialize RPI Cost       [Array for accumulating total cost]
Initialize RPI            [Array for weighted costs]
Initialize GPI            [Array for GPI]
Initialize REC            [Variable for number of records in table]
Set REC = total number of records in table
For n = 1 to REC          [Tally total cost and total units per GPI]
If GPI(n) = GPI(n+1) then
    RPI Units = RPI Units + RPI Units(n)
    RPI Cost = RPI Cost + RPI Cost(n)
Else                      [Store GPI and associated weighted cost]
    RPI(n) = (RPI Cost + RPI Cost(n)) / (RPI Units + RPI Units(n))
    GPI(n) = GPI
    Initialize RPI Units
    Initialize RPI Cost
Next n
```

The above approach causes the RPI (or weighted cost) to take into account the latest cost figures and number of units available for each drug from each distributor of the drug, resulting in a reference price that reflects the actual cost and availability of the drug in the market. Once the RPIs (or weighted costs) have been calculated for the GPIs, including brand-name and generic, these RPIs (or weighted costs) may be linked or otherwise associated with each drug by cross referencing the GPI for that drug, and hence the RPI for that drug, to the NDC for the drug. This allows each NDC to be associated with a corresponding RPI for purposes of adjudicating pharmacy claims and requesting reimbursement from plan clients.

In some implementations, the RPI for a given distributor's pricing and availability file may need to be adjusted to account for any differences and variations among distributors. For example, some distributors may include a pharmacy's entire discount in the list price provided in the pricing and availability data file, while others may not. To account for these differences, as mentioned above, a Wholesaler Adjustment Factor (WAFM) may be determined for a given distributor. To determine the WAFM, the distributor is asked to attest to the additional discounts obtained over the list price. For example, if a pharmacy can obtain the product at a 5% discount over list price, a 0.95 factor is utilized for the entire price file. The discount could also vary per product type, for example a brand or generic discount, and this WAFM could differ based on product type. Note that by default the adjustment factor may be set to 1 to reflect a presumption that no adjustment is needed to the RPI, but may thereafter be overridden, either automatically or manually by the user, when differences are detected in distributor packaging interpretations or other variations.

In a similar manner, in some implementations, the RPI for a given GPI may also need to be adjusted to account for differences and variations in price discounts among distributors. To account for any additional discounts on drugs provided to distributors, as mentioned above, a cost adjustment factor may be determined on a GPI basis and used to adjust the RPI for a given GPI. Additionally, to determine cost adjustment factor that might be applied to a given drug, the distributor's reported package WAC or AWP for the drug may be compared against Medi-Span's WAC or AWP per package. If the variance is determined to be significant (i.e., exceeding 50%), an adjustment factor may be applied to the package size. For example, if a bundle of 3 packages of 100 units is the basis for the reported AAC, and Medi-Span reports a package size of 100, an adjustment factor of 300 may be applied to the package quantity so that the AAC is divided by 300, rather than 100, to determine the AAC per unit. As before, this cost adjustment factor may be applied (e.g., multiplied) to the RPI to adjust the RPI for any additional discounts on drugs provided to distributors. Again, note that by default the cost adjustment factor may be set to 1 to reflect a presumption that no adjustment is needed to the RPI, but may thereafter be overridden, either automatically or manually by the user, when there are any additional discounts on drugs provided to distributors.

Once the foregoing calculations have been performed, preferably on a regular basis (e.g., hourly, daily, weekly, etc.), the resulting RPIs (including any adjustments thereto) may be uploaded to the PCM claims engine 202 (see FIG. 2) for use in adjudicating the claims submitted by the pharmacies 104. In some embodiments, the PCM application 318 may perform the uploading automatically so that little or no user involvement is required. In other embodiments, a user may manually initiate the process of uploading the RPIs to the PCM claims engine 202 using an appropriate graphical user interface.

FIGS. 6-9 illustrate examples of graphical user interfaces that may be used by the user to upload the RPIs to the PCM claims engine 202 and perform other functions according to the exemplary disclosed embodiments. The exemplary graphical user interfaces shown in FIGS. 6-9 are Web-based graphical user interfaces that may be accessed using any suitable Web browser after the appropriate authentication has been provided. Although these exemplary graphical user interfaces provide a needed function herein, they are by no means exclusive or exhaustive and additional or alternative graphical user interfaces may certainly be used. Similarly, the look and feel of these exemplary graphical user interfaces is illustrative only and variations in the layout, color scheme, graphics, and other design elements are certainly within the scope of the exemplary disclosed embodiments.

Figure 6:
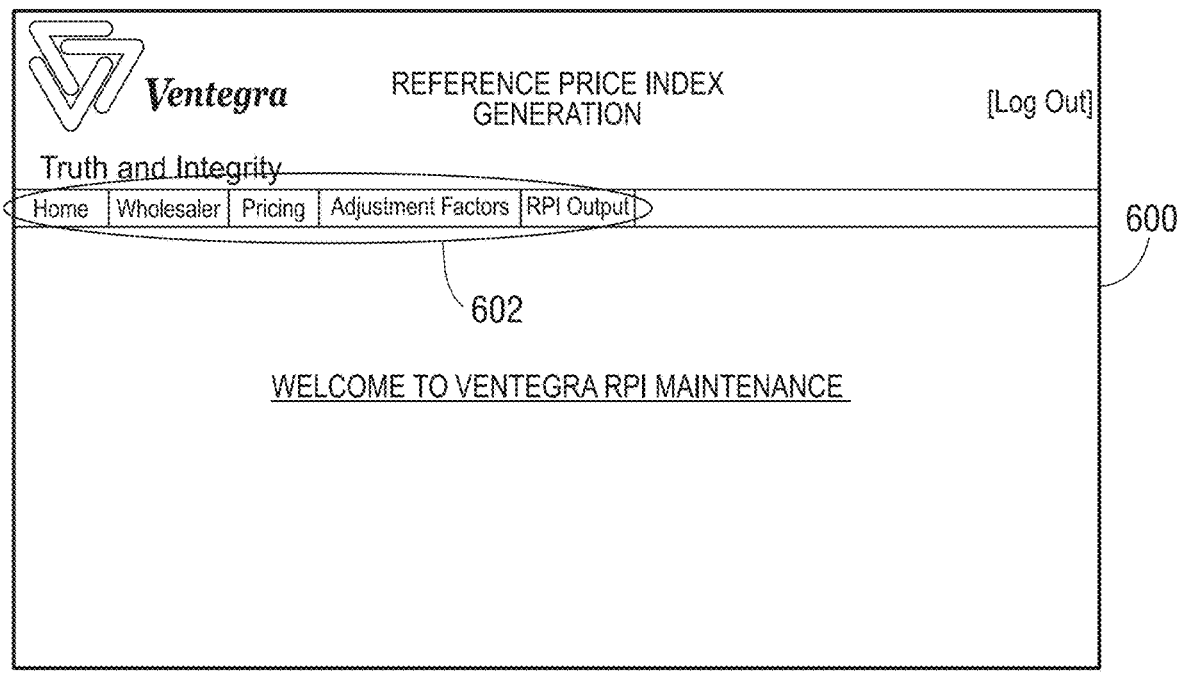
FIG. 6 is an example of a user interface that may be used to implement the PCM according to the exemplary disclosed embodiments.

Referring first to FIG. 6, an example of a graphical user interface 600 is shown that may be used as the main or home screen for the PCM application 318. As can be seen, the main screen 600 includes a plurality of tabs 602 that lead to additional screens (not expressly shown here) from which the user may access various features and functions of the PCM application 318. The user may navigate to one of these additional screens by selecting an appropriate tab 602, either from the main screen 600 or from one of the additional screens, to access these other features and functions.

Figure 7:
FIG. 7 is an example of another user interface that may be used to implement the PCM according to the exemplary disclosed embodiments.

One of the functions that the user may access from the main screen 600 is a data import screen, an example of which is depicted in FIG. 7 at 700. From this data import screen 700, the user may import data files from various distributors containing the pricing and availability data used by the PCM application 318 to calculate the RPIs, as mentioned above. To facilitate importing the data files, the data import screen 700 may be provided with a plurality of selection fields, including a source identifier field 702 that allows the user to assign a particular distributor to a given data file. The data import screen 700 may further include a file selection fields 704 that allows the user to select the data file to be imported. Clicking on an upload button 706 imports the distributor's data file into the aggregated pricing and availability database, overriding any existing data for that distributor. A data import table 708 shows some of the imported data, including the date imported at 710, the person who imported the data at 712, and the distributor who provided data at 714.

Figure 8:
FIG. 8 is an example of yet another user interface that may be used to implement the PCM according to the exemplary disclosed embodiments.

FIG. 8 illustrates an example of a reference price output screen 800 that the user may access to view the reference prices uploaded to the PCM claims engine 202. From this reference price output screen 800, the user may view the reference prices for every drug imported into the aggregated database. In addition, a plurality of search fields, including a source identifier field 802, a date uploaded field 804, a brand versus generic field 806, and an NDC code field 808, allow the user to filter the reference prices by specific criteria. Clicking on an apply button 810 applies the filter criteria the user specified and presents the results in reference price table 812. In the example shown here, the reference prices are shown according to brand versus generic at 814, NDC code 816, and reference price per unit at 818.

Figure 9:
FIG. 9 is an example of still another user interface that may be used to implement the PCM according to the exemplary disclosed embodiments.

FIG. 9 illustrates an example of an adjustment factor screen 900 that the user may access to view the packaging adjustment factor and cost adjustment factor applied to the references prices. From this adjustment factor screen 900, the user may use a plurality of search fields, including a source identifier field 902 and an NDC code field 904 to filter adjustment factors that were applied to the reference prices. Clicking on an apply button 906 applies the filter criteria the user specified and presents the results in an adjustment factor table 908. In this example, the adjustment factor table 908 shows the search results by NDC code at 910, the cost adjustment factor at 912, the numerator for the packaging adjustment factor at 914, and the denominator for the packaging adjustment factor at 916. The numerator and denominator adjustment factors are used to correct for different bulk package quantities used by wholesaler systems. These numerator and denominator adjustment factors together make up the Wholesale Adjustment Factor and may be derived manually or automatically. For example, a drug with a "unit" RPI that reflects one injector kit containing 2 syringes may be stored at the wholesaler in an "over-wrap" that, for each unit, contains 2 cases of product, with each case containing 4 trays of 10 kits of drug, each of which contains 2 syringes of active ingredient. In this example, the numerator would be 2 and the denominator would be 80, as pharmacies would be submitting one "unit" being assumed to equal one kit. Such Wholesale Adjustment Factors allow for correct calculation and adjustment of wholesaler storage sizes into the cost per unit necessary for application within the RPI. The user may edit or delete any of these adjustment factors by clicking on an edit or delete hyperlink, respectively, at 918, and may also add a new adjustment factor by clicking on the designated hyperlink for adding a new adjustment factor at 920.

While particular aspects, implementations, and applications of the present disclosure have been illustrated and described, it is to be understood that the present disclosure is not limited to the precise construction and compositions disclosed herein and that various modifications, changes, and variations may be apparent from the foregoing descriptions without departing from the spirit and scope of the exemplary disclosed embodiments as defined in the appended claims.

What is claimed is:

1. A computer-based method of implementing a pharmacy care manager (PCM), comprising:

receiving disparate pricing and availability data for pharmaceutical products from computing systems at multiple distributors of the pharmaceutical products through a data input unit in communication with a central processing unit, the disparate pricing and availability data received from the computing systems including Quantity on Hand (QOH), Actual Acquisition Cost (AAC), Wholesale Acquisition Cost (WAC), and Average Wholesale Price (AWP) for each pharmaceutical product from each distributor;

receiving from the computing systems identification data including Package Size for the pharmaceutical products from a publisher of the identification data through the data input unit in communication with the central processing unit; and executing by the central processing unit a PCM application stored on a data storage unit, the PCM application causing the central processing unit to automatically filter the disparate data received from the computing systems to remove unneeded data and sort the remaining data into standardized groups, automatically transform the data to a reference price index (RPI) for each pharmaceutical product, including automatically adding the AAC, WAC, or AWP for each pharmaceutical product, and automatically dividing the total by the QOH times the Package Size for each pharmaceutical product, the RPI representing a weighted cost that takes into account the latest cost and number of units available for each pharmaceutical product from each distributor thereof, resulting in reference prices that reflect actual cost and availability of the pharmaceutical product in the market, and using the RPI as a basis to automatically calculate a reference price for the pharmaceutical product and automatically uploading the calculated reference price to a PCM claims engine on a regularly scheduled basis;

wherein the PCM application, when executed by the central processing unit, further causes a payment equal to the calculated reference price to be sent to an external pharmacy via the central processing unit, and causes a request to be sent to an external plan client for reimbursement of the reference price via the central processing unit.

2. The computer-based method of claim 1, wherein the identification data for the pharmaceutical product includes a Generic Product Aggregator (GPA) and the central processing unit executes the PCM application to calculate the RPI for each pharmaceutical product according to the GPA for the pharmaceutical product.

3. The computer-based method of claim 2, further comprising using the central processing unit to execute the PCM application to calculate the RPI for each pharmaceutical product on a brand name pharmaceutical product and a generic pharmaceutical product basis.

4. The computer-based method of claim 1, further comprising using the central processing unit to execute the PCM application to set the reference price equal to the RPI for the pharmaceutical product.

5. The computer-based method of claim 1, further comprising using the central processing unit to execute the PCM application to apply a cost adjustment factor to the RPI for each pharmaceutical product.

6. The computer-based method of claim 1, further comprising using the central processing unit to execute the PCM application to apply a packaging adjustment factor to the RPI for each pharmaceutical product.

7. The computer-based method of claim 1, wherein the distributors of the pharmaceutical products include any one or any combination of the following: drug manufacturers, contract manufacturers, repackagers, drug wholesalers, third party logistics firms, and pharmacies.

8. A system for back-end adjusting of pharmaceutical product pricing from multiple different providers to account for differences in drug package sizes, comprising:

a central processing unit;

a display in data communication with the central processing unit; and a storage device in data communication with the central processing unit, the storage device storing computer-readable instructions for a pharmacy care manager (PCM) application that, when executed by the central processing unit, causes the system to:

receive disparate pricing and availability data for pharmaceutical products from computing systems at multiple distributors of the pharmaceutical products through a data input unit in communication with a central processing unit, the disparate pricing and availability data received from the computing systems including Quantity on Hand (QOH), Actual Acquisition Cost (AAC), Wholesale Acquisition Cost (WAC), and Average Wholesale Price (AWP) for each pharmaceutical product from each distributor;

receive from the computing systems identification data including Package Size for the pharmaceutical products from a publisher of the identification data through the data input unit in communication with the central processing unit;

automatically filter the disparate data received from the computing systems to remove unneeded data and sort the remaining data into standardized groups, automatically transform the data to a reference price index (RPI) for each pharmaceutical product, including automatically adding the AAC, WAC, or AWP for each pharmaceutical product, and automatically dividing the total by the QOH times the Package Size for each pharmaceutical product, the RPI representing a weighted cost that takes into account the latest cost and number of units available for each pharmaceutical product from each distributor thereof, resulting in reference prices that reflect actual cost and availability of the pharmaceutical product in the market, and using the RPI as a basis to automatically calculate a reference price for the pharmaceutical product and automatically upload the calculated reference price to a PCM claims engine on a regularly scheduled basis; and cause a payment equal to the calculated reference price to be sent to an external pharmacy via the central processing unit, and causes a request to be sent to an external plan client for reimbursement of the reference price via the central processing unit.

9. The system of claim 8, wherein the pharmaceutical product data file for the given drug includes identification data for the given drug, the identification data including a Generic Product Aggregator (GPA), and wherein the reference price for the given drug was determined based on the GPA for the pharmaceutical product.

10. The system of claim 8, wherein the reference price for the given drug was determined on a brand name pharmaceutical product and a generic pharmaceutical product basis.

11. The system of claim 8, wherein the reference price for the given drug was set equal to a Reference Price Index (RPI) for the pharmaceutical product.

12. The system of claim 8, wherein the reference price for the given drug reflects application of the cost adjustment factor to the RPI for the given drug.

13. The system of claim 8, wherein the reference price for the given drug reflects application of the packaging adjustment factor to the RPI for the given drug.

14. The system of claim 8, wherein the source identifier field of the data import screen allows the user to select from one of the pharmaceutical products include any one or any combination of the following: drug manufacturers, contract manufacturers, repackagers, drug wholesalers, third party logistics firms and pharmacies.

* * * * *